(12) United States Patent
Maiorino et al.

(10) Patent No.: US 10,912,552 B2
(45) Date of Patent: Feb. 9, 2021

(54) TAPERED LOOPED SUTURE

(71) Applicant: Covidien LP, Mansfield, MA (US)

(72) Inventors: Nicholas Maiorino, Branford, CT (US); William R. Bowns, Ansonia, CT (US)

(73) Assignee: Covidien LP, Mansfield, MA (US)

( * ) Notice: Subject to any disclaimer, the term of this patent is extended or adjusted under 35 U.S.C. 154(b) by 247 days.

(21) Appl. No.: 16/006,886

(22) Filed: Jun. 13, 2018

(65) Prior Publication Data

US 2018/0289368 A1 Oct. 11, 2018

Related U.S. Application Data

(62) Division of application No. 12/548,594, filed on Aug. 27, 2009, now Pat. No. 10,016,196.

(60) Provisional application No. 61/096,145, filed on Sep. 11, 2008.

(51) Int. Cl.
*A61B 17/06* (2006.01)
*A61B 17/04* (2006.01)

(52) U.S. Cl.
CPC .. *A61B 17/06166* (2013.01); *A61B 17/06195* (2013.01); *A61B 2017/0477* (2013.01); *A61B 2017/0496* (2013.01); *A61B 2017/06176* (2013.01)

(58) Field of Classification Search
CPC .............. A61B 17/06166; A61B 17/04; A61B 2017/06171; A61B 2017/06176; A61B 2017/0618; A61B 2017/06185; A61B 2017/0619; A61B 2017/06052
See application file for complete search history.

(56) References Cited

U.S. PATENT DOCUMENTS

| | | |
|---|---|---|
| 2,514,184 A | 7/1950 | Lower |
| 3,513,848 A | 5/1970 | Garvey |
| 3,657,056 A | 4/1972 | Winston et al. |
| 3,874,963 A | 4/1975 | Barger |
| 4,662,068 A | 5/1987 | Polonsky |
| 4,950,285 A | 8/1990 | Wilk |
| 5,002,563 A | 3/1991 | Pyka et al. |

(Continued)

FOREIGN PATENT DOCUMENTS

| | | |
|---|---|---|
| EP | 0870471 A1 | 10/1998 |
| EP | 2163207 A1 | 3/2010 |

(Continued)

OTHER PUBLICATIONS

Canadian Office Action from corresponding Canadian Application No. 2,678,277 dated Aug. 28, 2015.

(Continued)

*Primary Examiner* — Erich G Herbermann
(74) *Attorney, Agent, or Firm* — Carter, DeLuca & Farrell LLP (57) ABSTRACT

A suture including a loop having a tapered surface is provided. The suture includes an elongate body including a proximal portion and a distal portion, wherein the distal portion includes first and second overlapping sections and a loop. A proximal end of the first overlapping section may be tapered with respect to a longitudinal axis of the elongate body. The first overlapping section may be secured to the second overlapping section proximal of the loop. The overlapping sections may be secured together by at least one method selected from the group consisting of glues, adhesives, epoxies, solvents, heat and ultrasonic energy.

20 Claims, 5 Drawing Sheets

(56) References Cited

U.S. PATENT DOCUMENTS

| | | |
|---|---|---|
| 5,123,913 A | 6/1992 | Wilk et al. |
| 5,226,535 A | 7/1993 | Rosdhy et al. |
| 5,259,846 A | 11/1993 | Granger et al. |
| 5,383,905 A | 1/1995 | Golds et al. |
| 5,403,331 A | 4/1995 | Chesterfield et al. |
| 5,417,700 A | 5/1995 | Egan |
| 5,683,417 A | 11/1997 | Cooper |
| 5,830,234 A | 11/1998 | Wojciechowicz et al. |
| 5,893,880 A | 4/1999 | Egan et al. |
| 5,964,765 A | 10/1999 | Fenton, Jr. et al. |
| 5,968,077 A | 10/1999 | Wojciechowicz et al. |
| 6,077,277 A | 6/2000 | Mollenauer et al. |
| 6,089,438 A | 7/2000 | Suzuki et al. |
| 6,174,324 B1 | 1/2001 | Egan et al. |
| 6,217,591 B1 | 4/2001 | Egan et al. |
| 6,286,746 B1 | 9/2001 | Egan et al. |
| 6,296,859 B1 | 10/2001 | Foersteer |
| 6,358,271 B1 | 3/2002 | Egan et al. |
| 6,409,743 B1 | 6/2002 | Fenton, Jr. |
| 6,436,099 B1 | 8/2002 | Drewry et al. |
| 6,488,690 B1 | 12/2002 | Morris et al. |
| 6,547,807 B2 | 4/2003 | Chan et al. |
| 6,669,705 B2 | 12/2003 | Westhaver et al. |
| 7,090,111 B2 | 8/2006 | Egan et al. |
| 7,429,266 B2 | 9/2008 | Bonutti et al. |
| 7,533,791 B2 | 5/2009 | Steiner et al. |
| 7,582,097 B2 | 9/2009 | McRury et al. |
| 10,016,196 B2 | 7/2018 | Maiorino et al. |
| 2002/0011508 A1 | 1/2002 | Egan et al. |
| 2002/0029065 A1 | 3/2002 | Shchervinsky |
| 2003/0191479 A1 | 10/2003 | Thornton |
| 2004/0122451 A1 | 6/2004 | Wood |
| 2005/0165448 A1 | 7/2005 | Egan et al. |
| 2005/0216058 A1 | 9/2005 | Egan et al. |
| 2005/0267531 A1 | 12/2005 | Ruff et al. |
| 2005/0277984 A1 | 12/2005 | Long |
| 2006/0025858 A1 | 2/2006 | Alameddine |
| 2006/0116718 A1 | 6/2006 | Leiboff |
| 2006/0259076 A1 | 11/2006 | Burkhart et al. |
| 2008/0281357 A1 | 11/2008 | Sung et al. |
| 2009/0216269 A1 | 8/2009 | Harrington et al. |
| 2009/0248070 A1 | 10/2009 | Kosa et al. |
| 2009/0259251 A1 | 10/2009 | Cohen |
| 2009/0299407 A1 | 12/2009 | Yuan et al. |
| 2010/0204730 A1 | 8/2010 | Maiorino et al. |
| 2010/0274283 A1 | 10/2010 | Kirsch et al. |

FOREIGN PATENT DOCUMENTS

| | | |
|---|---|---|
| EP | 2184157 A1 | 5/2010 |
| FR | 2729940 A1 | 8/1996 |
| JP | 9155979 | 6/1997 |
| WO | 9625109 A1 | 8/1996 |
| WO | 9909891 A1 | 3/1999 |
| WO | 9926542 A1 | 6/1999 |
| WO | 9952451 A1 | 10/1999 |
| WO | 0222025 A1 | 3/2002 |
| WO | 03088818 A2 | 10/2003 |
| WO | 2005112787 A2 | 12/2005 |
| WO | 2008013864 A2 | 1/2008 |

OTHER PUBLICATIONS

European Examination Report issued in corresponding European Application No. 14181296.6 dated Nov. 5, 2015.

European Office Action dated Feb. 7, 2017 issued in EP Application No. 14 163 490.

European Search Report for EP 12186217.1-2310 date of completion is Nov. 6, 2012 (9 pages).

Lendlein A. et al., "Shape-Memory Polymers", Angewandte Chemie International Edition, vol. 41, No. 12, Jun. 17, 2002, pp. 2034-2057.

European Search Report EP 14181296.6-1654 date of completion Oct. 16, 2014.

European Search Report EP14163490.7-1654 dated Jun. 3, 2014.

TAPERED LOOPED SUTURE

CROSS-REFERENCE TO RELATED APPLICATION

The present application is a divisional of U.S. patent application Ser. No. 12/548,594 filed Aug. 27, 2009, which claims the benefit of and priority to U.S. Provisional Application Ser. No. 61/096,145, filed Sep. 11, 2008, and the disclosures of each of the above-identified applications are hereby incorporated by reference in their entirety

BACKGROUND

Technical Field

The present disclosure relates to a suture having a loop. More particularly, the present disclosure relates to a looped suture having a tapered surface.

Background of Related Art

Sutures including loops formed therein are known. A loop formed in a suture during manufacture may be used to secure the suture to tissue. Regardless of the reason for forming the loop, when a loop is formed in a suture, whether using adhesive, heat or ultrasonic energy, the diameter of the suture is doubled where the two suture portions overlap. In the event that the suture loop is used to secure tissue, the doubling of the diameter of the suture in order to create the loop may increase the amount of force necessary to pull the loop through tissue. This increased force applied to the suture may result in tearing or other unnecessary trauma to the tissue being sutured. Therefore, it would be beneficial to have a looped suture to include a tapered surface and methods of making such a suture.

SUMMARY

A suture including a loop having a tapered surface is provided. The suture includes an elongate body including a proximal portion and a distal portion, wherein the distal portion of the elongate body includes first and second overlapping sections and a loop. A proximal end of the first overlapping section may include a tapered surface which is tapered with respect to a longitudinal axis of the elongate body. The first overlapping section may be secured to the elongate body proximal of the loop. The overlapping sections may be secured together by at least one method selected from the group consisting of glues, adhesives, epoxies, solvents, heat and ultrasonic energy.

The overlapping sections may be welded together using ultrasonic energy. The overlapping sections may instead be adhered together using an adhesive. The tapered surface may be generally linear or curved. The curve may be convex or concave. The tapered surface may be angled downwards towards a longitudinal axis of the elongate body. The loop may be sized and dimensioned to receive a length of the elongate body. The loop may be sized and dimensioned to receive a surgical needle.

The suture may further include a surgical needle on a proximal end of the elongate body. The elongate body may include barbs on at least a portion thereof. The loop may include barbs on at least a portion thereof. The tapered surface may be configured to penetrate tissue. The tapered surface may form an angle of about zero degrees (0°) to about ninety degrees (90°) relative to a longitudinal axis of the elongated body, preferably, about five degrees (5°) to about sixty degrees (60°). The suture may be selected from the group consisting of monofilament and multifilament.

Also provided is a method of using a looped suture including a tapered surface. The method includes the steps of providing a suture including an elongate body, and a loop formed on a distal end of the elongated body, wherein at least a portion of the elongate body is secured to an overlapping section and a proximal end of the overlapping section is tapered, inserting a proximal end of the elongate body into tissue, and pulling the elongate body through the tissue until the tapered overlapping section engages the tissue.

The method further includes the step of inserting the proximal end of the elongate body through the loop. The suture may include a needle on the proximal end of the elongate body. The method may also include the step of tensioning the proximal end of the elongate body through the loop until the tissue is retained within the suture.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
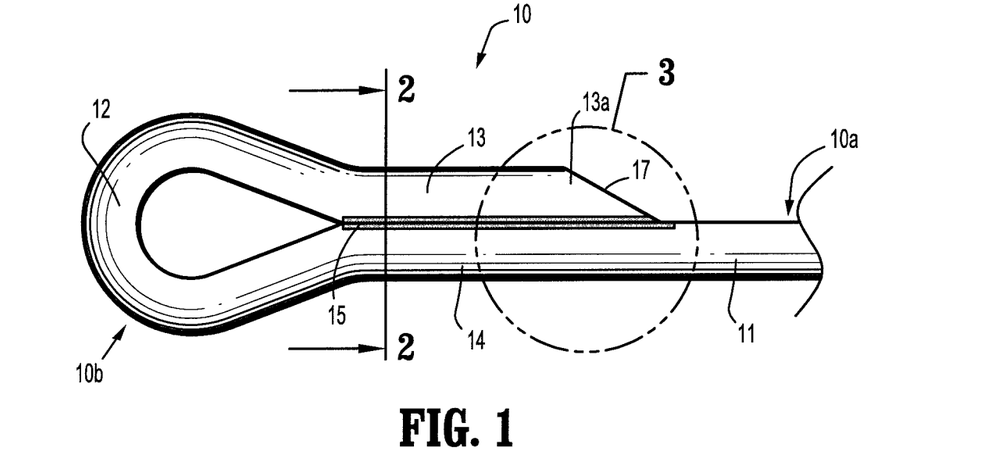
FIG. 1 is a side view of a looped suture in accordance with one embodiment of the present disclosure.

As shown in FIG. 1, an embodiment of a suture according to the present disclosure is shown generally as looped suture 10. Suture 10 is formed from a monofilament thread 11; however, it is envisioned that suture 10 may be formed from braided threads, multifilament threads and other surgical fibers.

Figure 4A:
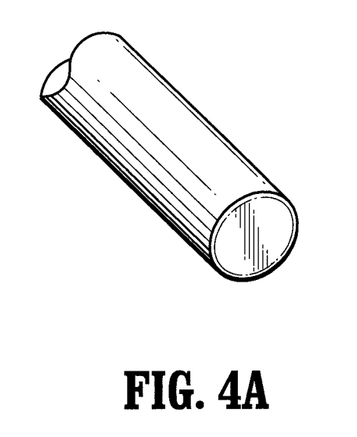
FIGS. 4A-4F are perspective views of a thread having a circular (FIG. 4A), elliptical (FIG. 4B), rectangular (square) (FIG. 4C), flat (FIG. 4D), octagonal (FIG. 4E), and rectangular (FIG. 4F) cross-sectional profiles.
Figure 4B:
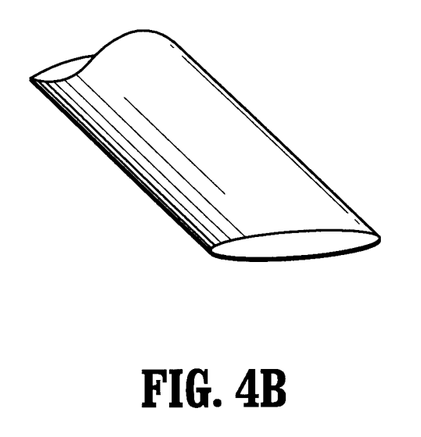
Figure 4C:
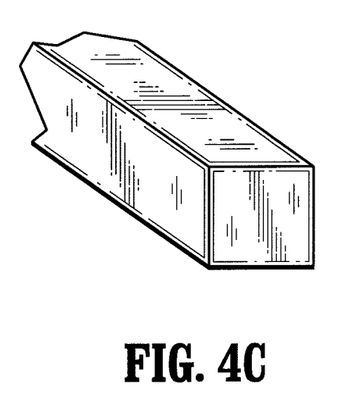
Figure 4D:
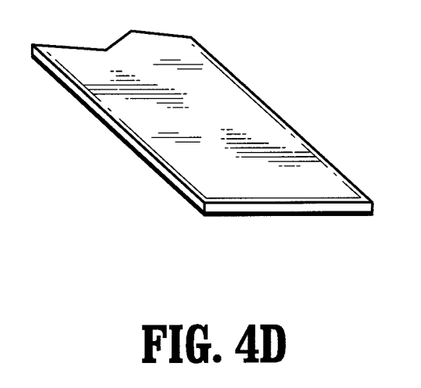
Figure 4E:
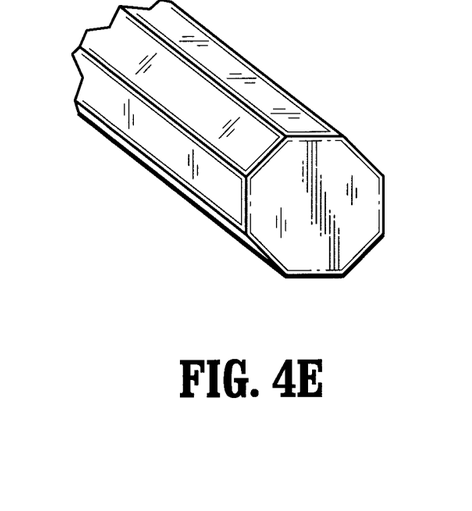
Figure 4F:
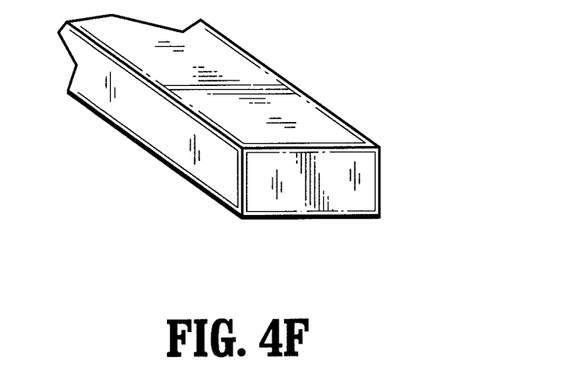
Figure 5A:
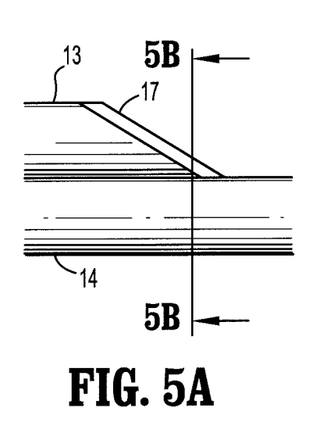
FIG. 5A-5C are views of an alternate embodiment of a looped suture of the present disclosure.
Figure 5B:
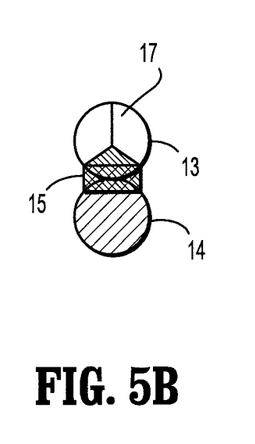
Figure 5C:
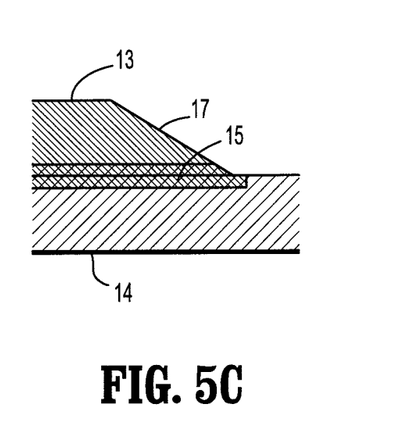
Figure 6A:
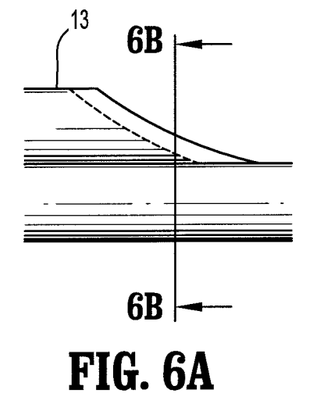
FIG. 6A-6C are views of yet another embodiment of a looped suture of the present disclosure.
Figure 6B:
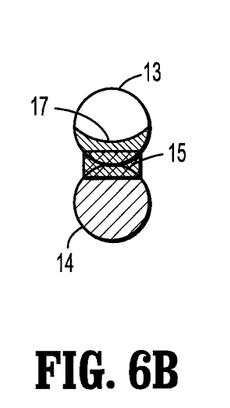
Figure 6C:
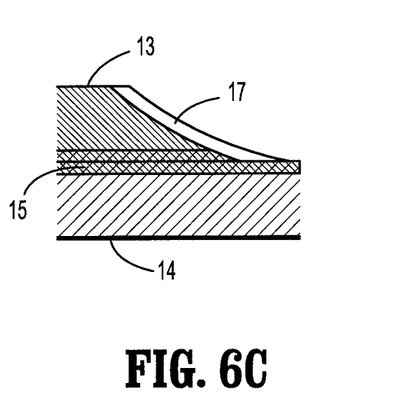
Figure 7A:
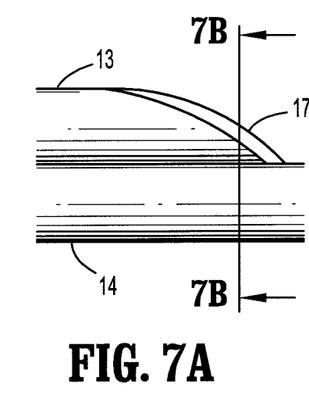
FIGS. 7A-7C are views of still another embodiment of a looped suture of the present disclosure.
Figure 7B:
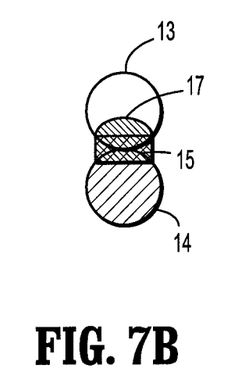
Figure 7C:
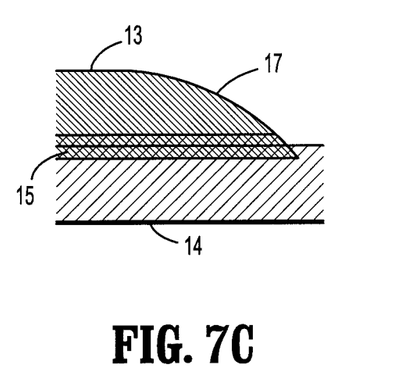

Although shown having a circular cross-sectional geometry, the cross-sectional geometry of thread 11 may be of any suitable shape. For example, FIGS. 4A-4F illustrate cross-sectional views of alternative embodiments of the various cross-sectional geometries of thread 11, namely, round (FIG. 4A), elliptical (FIG. 4B), square (FIG. 4C), flat (FIG. 4D), octagonal (FIG. 4E), and rectangular (FIG. 4F).

Thread 11 may be formed of degradable materials, non-degradable materials, and combinations thereof. More particularly, thread 11 may be formed of a degradable material selected from the group consisting of polyesters, polyorthoesters, polymer drugs, polyhydroxybutyrates, lactones, proteins, cat gut, collagens, carbonates, homopolymers thereof, copolymers thereof, and combinations thereof. In other embodiments, suitable degradable materials which may be utilized to form thread 11 include natural collagenous materials or synthetic resins including those derived from alkylene carbonates such as trimethylene carbonate, tetramethylene carbonate, and the like; caprolactone; dioxanone; glycolic acid; lactic acid; homopolymers thereof; copolymers thereof; and combinations thereof. In some embodiments, glycolide and lactide based polyesters, especially copolymers of glycolide and lactide, may be utilized to form thread 11.

Suitable non-degradable materials which may be utilized to form thread 11 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, cotton, linen, carbon fibers, and the like. The polypropylene may be isotactic polypropylene or a mixture of isotactic and syndiotactic or atactic polypropylene.

Thread 11 may be formed using any technique within the purview of those skilled in the art, such as, for example, extrusion, molding and/or spinning. In some embodiments, thread 11 may include a yarn made of more than one filament, which may contain multiple filaments of the same or different materials. Where thread 11 is made of multiple filaments, thread 11 may be made using any known technique such as, for example, braiding, weaving or knitting. Threads 11 may also be combined to produce a non-woven suture. Threads 11 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

Still referring to FIG. 1, looped suture 10 includes a loop 12 formed on a distal end 10b thereof. Proximal end 10a of looped suture 10 may include one or more suture needles (not shown). Loop 12 forms a substantially teardrop shape and may be of any size. In one embodiment, loop 12 is sized to receive proximal end 10a of looped suture 10. A first section 13 of monofilament thread 11 overlays a second section 14 of thread 11 to form loop 12. The adjacent surfaces of first and second sections 13, 14 form a joined segment or joint 15.

In one embodiment, first and second sections 13, 14 of thread 11 are welded together as disclosed in U.S. Provisional Application No. 61/099,594, filed Sep. 24, 2008, the entire content of which is incorporated by reference herein. In this manner, first and second sections 13, 14 of thread 11 are locally heated until each fuses to form weld segment 15. Various types of energy may be used to locally heat first and second sections 13, 14 to form joined segment 15, including, radio frequency (RF), ultrasonic, laser, electrical arc discharge, and thermal. Alternatively, first and second sections 13, 14 of thread 11 may be joined using glues, epoxies, solvents, or other adhesives.

Figure 3:
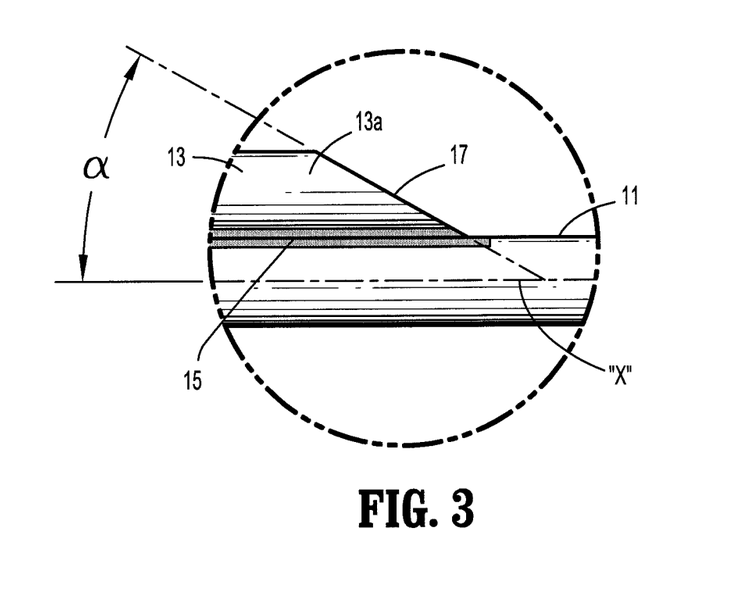
FIG. 3 is an enlarged side view of portion 3 of FIG. 1.

With particular reference to FIG. 3, a proximal end 13a of first section 13 is angled to form a tapered surface 17. Tapered surface 17 angles downwardly towards proximal end 10a of looped suture 10. Tapered surface 17 forms an angle α relative to a longitudinal axis "X" of second section 14, between zero degrees (0°) and ninety degrees (90°), and preferably between about five degrees (5°) to about sixty degrees (60°). Tapered surface 17 facilitates insertion of loop 12 into or through tissue. Tapered surface 17 may be formed prior to, during or following the joining of first and second sections 13, 14. In one embodiment, tapered surface 17 is formed during the welding process using a die (not shown) having a cutting surface (not shown). In another embodiment, tapered surface 17 is formed by a blade (not shown). The blade used to form tapered surface 17 may be heated, ultrasonically vibrated or otherwise adapted to facilitate cutting of thread 11. Tapered surface 17 of first section 13 may be formed such that joined segment 15 extends beyond first section 13 of thread 11. In this manner, tapered surface 17 forms a smooth transition with second section 14 of thread 11, thereby decreasing the likelihood that first and second sections 13, 14 might separate or peel away from each other as looped suture 10 is pulled through tissue.

Although shown having a substantially planar taper, tapered surface 17 may include any number of configurations. For example, FIGS. 5A-7C illustrate alternate embodiments, including a beveled tapered surface 17a (FIGS. 5A-5C), a laterally and longitudinally concave tapered surface 17b (FIGS. 6A-6C), a laterally and longitudinally convex tapered surface 17c (FIGS. 7A-7C) or any combination thereof. Respective beveled, concave and convex tapered surfaces (collectively, contoured tapered surfaces 17a-c) may be formed in a similar manner as planar tapered surface 17. That is, contoured tapered surfaces 17a-c may be formed during the welding process using a die (not shown) having an appropriately shaped cutting surface (not shown). Alternatively, contoured tapered surfaces 17a-c may be formed using a blade (not shown) having an appropriately shaped cutting surface. Tapered surface 17 may be selected depending on the tissue being sutured and/or the desired depth of penetration of loop 12 within the tissue.

Figure 1A:
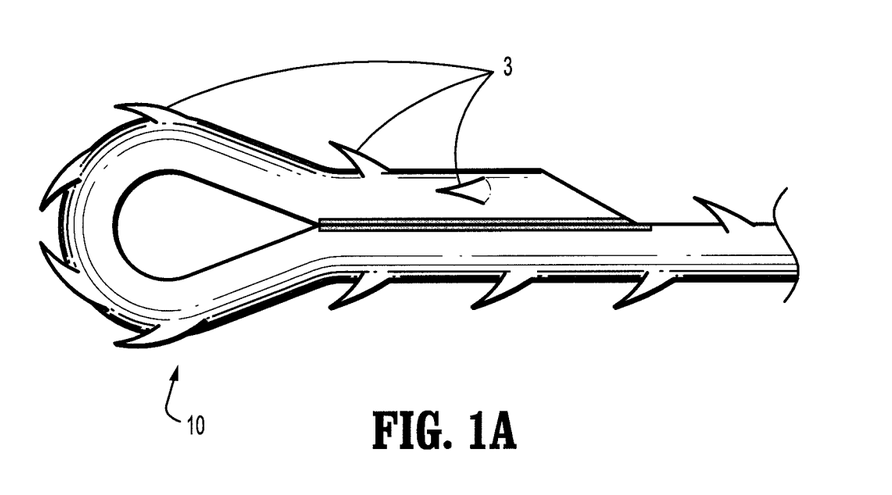
FIG. 1A is a side view of a looped suture in accordance with another embodiment of the present disclosure.
Figure 2:
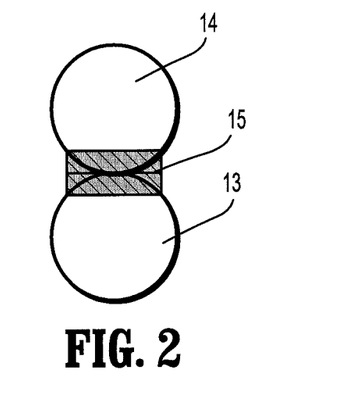
FIG. 2 is a cross-sectional end view of the looped suture taken along line 2-2 of FIG. 1.

Turning briefly to FIG. 1A, looped suture 10 may include barbs 3 or other projections formed therein. Barbs 3 may be arranged in any suitable pattern, for example, helical, linear, or randomly spaced. The pattern may be symmetrical or asymmetrical. The number, configuration, spacing and surface area of barbs 3 may vary depending upon the tissue in which suture 10 is used, as well as the composition and geometry of the material of thread 11. Additionally, the proportions of barbs 3 may remain relatively constant while the overall length of barbs 3 and the spacing of barbs 3 may be determined by the tissue being connected. For example, if suture 10 is to be used to connect the edges of a wound in skin or tendon, barbs 3 may be made relatively short and more rigid to facilitate entry into this rather firm tissue. Alternatively, if suture 10 is intended for use in fatty tissue, which is relatively soft, barbs 3 may be made longer and spaced further apart to increase the ability of suture 10 to grip the soft tissue.

The surface area of barbs 3 may also vary. For example, fuller-tipped barbs may be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In particular embodiments, a single directional suture may have both large and small barbs; in other embodiments a bi-directional suture may have both large and small barbs. Barbs 3 may include geometrical shapes such as round, triangular, square, oblique, elliptical, octagonal, rectangular, and flat. In some embodiments, barbs 3 may be formed on loop 12 which allows movement of loop 12 through tissue in one direction but resists the withdrawal of suture 10 after loop 12 has been implanted in the tissue.

When fabricated from a degradable material, suture 10 maintains its structural integrity after implantation for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc. The manufacturing parameters involved in the forming of loop 12 also affect the rate at which suture 10 is absorbed. Joint 15 may absorb at a different rate from the remainder of suture 10.

The formation of barbs 3 (FIG. 1A) on a suture body may be utilized to change the degradation time of suture 10 as described in U.S. patent application Ser. No. 11/556,002 filed on Nov. 2, 2006, entitled "Long Term Bioabsorbable Barbed Sutures", the entire contents of which are incorporated by reference herein.

Looped suture 10 may be coated or impregnated with one or more medico-surgically useful substances which accelerate or beneficially modify the healing process when suture 10 is applied to a wound or surgical site. In certain embodiments, a coating may be formed from degradable polymers selected from the group consisting of lactones, carbonates, polyorthoesters, hydroxyalkoanates, hydroxybutyrates, bioactive agents, polyanhydrides, silicone, calcium stearoyl lactylates, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, suture 10 can be provided with a bioactive agent that will be deposited at the sutured site. The bioactive agent can be chosen for its antimicrobial properties, capability for promoting wound repair and/or tissue growth, or for specific indications such as thrombosis. In embodiments, combinations of such agents may be applied to the medical device of the present disclosure before, during, or after formation of barbs 3.

The term "antimicrobial agent" as used herein includes an agent which by itself or through assisting the immune system, helps the body destroy or resist microorganisms that may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following bioactive agents may be used alone or in combination with other bioactive agents described herein: an anthracycline, doxorubicin, mitoxantrone, a fluoropyrimidine, a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, erythromycin, azithromycin, clindamycin, syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Other suitable bioactive agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly (ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, $\alpha,\alpha$-dipyridyl, $\beta$-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; $\beta$-Cyclodextrin Tetradecasulfate; Eponemycin; Camptothecin; Fumagillin Gold Sodium Thiomalate ("GST"); D-Penicillamine ("CDPT"); $\beta$-1-anticollagenase-serum; $\alpha$2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Suture 10 may also include, for example, biologically acceptable plasticizers, antioxidants and colorants, which may be impregnated into the filament(s) utilized to form a suture of the present disclosure or included in a coating thereon.

Bioactive agents may be applied onto suture 10 utilizing any method within the purview of one skilled in the art including, for example, dipping, spraying, vapor deposition, brushing, solvent evaporation, compounding and the like. In embodiments, a bioactive agent may be deposited within the barb angles, that is, the angle formed between barbs 3 and thread 11. This placement of the bioactive agent between barb 3 and thread 11 places the bioactive agent at precisely defined locations within a tissue wound closure, which thereby provides a unique controlled and sustained release dosage form.

Thread 11 may be dyed in order to increase the visibility of suture 10 in the surgical field. Any dye suitable for incorporation in medical devices may be used. Such dyes include, but are not limited to, carbon black, bone black, D&C Green No. 6, and D&C Violet No. 2. Filaments in accordance with the present disclosure may be dyed by adding dye in an amount up to about a few percent; in other embodiments, they may be dyed by adding dye in an amount of about 0.2%; in still further embodiments, the dye may be added in an amount from about 0.06% to about 0.08%.

In use, looped suture 10 includes a needle (not shown) on proximal end 10a thereof. The needle is inserted into and through a first and second flap of tissue. Looped suture 10 is pulled through the tissue until proximal end 13a of first section 13 contacts the tissue. Continued pulling on proximal end 10a of suture 10 causes tapered proximal end 13a to engage the tissue. Tapered surface 17 of proximal end 13a allows the overlapping section of suture 10 to be received within the tissue with reduced resistance while minimizing trauma to the tissue. Once a portion of loop 12 of suture 10 is received within the tissue, proximal end 10a of suture 10 may be inserted through loop 12. Proximal end 10a of suture 10 may then be pulled tight, thereby approximating the first and second tissue flaps towards one another. Proximal end 10a of suture 10 may then be knotted or otherwise secured to loop 12. In one embodiment, a knot may be formed in proximal end 10a to prevent proximal end 10a from withdrawing from loop 12. In another embodiment, proximal end 10a of suture 10 may be tied directly to loop 12.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of using a looped suture including a tapered surface, the method comprising:
   providing a suture including an elongate body, and a loop formed from a distal portion of the elongate body, wherein a section of the elongate body is secured to an overlapping section of the elongate body to form the loop, wherein a proximal end of the overlapping section is tapered;
   inserting a proximal portion of the elongate body into tissue;
   pulling the elongate body through the tissue until the tapered overlapping section engages the tissue;
   continuing pulling the elongate body through the tissue such that the tapered overlapping section is at least partially received within the tissue.

2. The method of claim 1, further including inserting the proximal portion of the elongate body through the loop.

3. The method of claim 2, further including tensioning the proximal portion of the elongate body through the loop until the tissue is retained within the suture.

4. The method of claim 1, wherein the suture includes a needle on the proximal portion of the elongate body.

5. The method of claim 1, further including forming a knot in the suture.

6. The method of claim 5, wherein forming the knot includes tying the knot near the proximal end of the elongate body to retain the proximal portion of the elongate body through the loop.

7. The method of claim 5, wherein forming the knot includes tying the proximal portion of the elongate body to the loop.

8. The method of claim 1, wherein the tapered proximal end is generally linear.

9. The method of claim 1, wherein the tapered proximal end is generally curved.

10. The method of claim 9, wherein the curve is convex.

11. The method of claim 9, wherein the curve is concave.

12. The method of claim 1, wherein the tapered proximal end angles downward towards a longitudinal axis of the elongate body.

13. The method of claim 12, wherein the tapered proximal end forms an angle of about zero degrees (0°) to about ninety degrees (90°) relative to the longitudinal axis of the elongate body.

14. The method of claim 13, where the tapered proximal end forms an angle of about five degrees (5°) to about sixty degrees (60°).

15. The method of claim 1, wherein the loop is sized and dimensioned to receive the proximal end of the elongate body.

16. The method of claim 1, wherein the loop is sized and dimensioned to receive a surgical needle.

17. The method of claim 1, wherein the elongate body includes barbs on at least a portion thereof.

18. The method of claim 1, wherein the loop includes barbs on at least a portion thereof.

19. The method of claim 1, wherein the tapered proximal end is configured to penetrate tissue.

20. The method of claim 1, wherein each of the section of elongate body and the overlapping section of the elongate body define a longitudinal axis, the longitudinal axis of the section of elongate body and the longitudinal axis of the overlapping section are parallel.

* * * * *